United States Patent
Waibel

(10) Patent No.: US 9,514,130 B2
(45) Date of Patent: *Dec. 6, 2016

(54) DEVICE FOR EXTRACTING INFORMATION FROM A DIALOG

(71) Applicant: Facebook, Inc., Menlo Park, CA (US)

(72) Inventor: Alexander Waibel, Murrysville, PA (US)

(73) Assignee: Facebook, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/985,300

(22) Filed: Dec. 30, 2015

(65) Prior Publication Data

US 2016/0110350 A1  Apr. 21, 2016

Related U.S. Application Data

(63) Continuation of application No. 13/760,535, filed on Feb. 6, 2013.

(60) Provisional application No. 61/608,334, filed on Mar. 8, 2012.

(51) Int. Cl.

| G06F 17/28 | (2006.01) |
| G10L 15/00 | (2013.01) |
| G10L 15/26 | (2006.01) |
| G10L 13/027 | (2013.01) |
| G10L 15/18 | (2013.01) |

(52) U.S. Cl.
CPC ........... *G06F 17/289* (2013.01); *G10L 13/027* (2013.01); *G10L 15/00* (2013.01); *G10L 15/1822* (2013.01); *G10L 15/26* (2013.01)

(58) Field of Classification Search
CPC .. G06F 17/289; G10L 2015/221; G10L 15/22; G10L 2015/226; G10L 13/033

USPC ........... 704/2, 7, 8, 200, 231, 251, 275, 277
See application file for complete search history.

(56) References Cited

U.S. PATENT DOCUMENTS

| 5,712,957 A | 1/1998 | Waibel et al. |
| 5,855,000 A | 12/1998 | Waibel et al. |
| 6,324,510 B1 | 11/2001 | Waibel et al. |
| 6,963,837 B1 | 11/2005 | Finke et al. |
| 7,124,085 B2 | 10/2006 | Junqua et al. |
| 7,149,347 B1 | 12/2006 | Wnek |
| 7,660,400 B2 | 2/2010 | Bangalore et al. |

(Continued)

FOREIGN PATENT DOCUMENTS

| JP | H11-120176 A | 4/1999 |
| JP | 2000-010578 A | 1/2000 |

(Continued)

OTHER PUBLICATIONS

Narayanan, S., et al.: "Transonics: a speech to speech system for English-Persian interactions", Automatic Speech Recognition and Understanding, 2003, ASRU 2003 IEEE Workshop on St. Thomas, VI, USA, Piscataway, NJ, USA, Nov. 30-Dec. 3, 2003, pp. 670-675.

(Continued)

*Primary Examiner* — Thierry L Pham
(74) *Attorney, Agent, or Firm* — Fenwick & West LLP

(57) ABSTRACT

Computer-implemented systems and methods for extracting information during a human-to-human mono-lingual or multi-lingual dialog between two speakers are disclosed. Information from either the recognized speech (or the translation thereof) by the second speaker and/or the recognized speech by the first speaker (or the translation thereof) is extracted. The extracted information is then entered into an electronic form stored in a data store.

20 Claims, 9 Drawing Sheets

(56) References Cited

U.S. PATENT DOCUMENTS

| | | | |
|---|---|---|---|
| 8,090,570 | B2 | 1/2012 | Waibel et al. |
| 8,204,739 | B2 | 6/2012 | Waibel et al. |
| 2006/0173682 | A1 | 8/2006 | Manabe et al. |
| 2007/0033005 | A1 | 2/2007 | Cristo et al. |
| 2007/0118351 | A1 | 5/2007 | Sumita |
| 2007/0271088 | A1 | 11/2007 | Waibel et al. |
| 2008/0077387 | A1 | 3/2008 | Ariu |
| 2008/0120091 | A1 | 5/2008 | Waibel et al. |
| 2008/0126087 | A1 | 5/2008 | Chou |
| 2008/0235014 | A1 | 9/2008 | Oz |
| 2010/0076972 | A1 | 3/2010 | Baron et al. |
| 2011/0307241 | A1 | 12/2011 | Waibel et al. |

FOREIGN PATENT DOCUMENTS

| | | |
|---|---|---|
| JP | 2005-141089 | 6/2005 |
| JP | 2011-524991 A | 9/2011 |

OTHER PUBLICATIONS

Azzini et al., "Application of Spoken Dialogue Technology in a Medical Domain", Text, Speech and Dialogue, Springer Berlin Heidelberg, Berlin, vol. 2448, Jan. 1, 2006, pp. 449-452.

Azzini et al., "First steps toward an adaptive spoken dialogue system in medical domain", Eurospeech, Scandinavia, vol. 2, Jan. 1, 2001, 4 pages.

Eck et al.: "Jibbigo: Speech-to-Speech translation on mobile devices", Spoken Language Technology Workshop (SLT), IEEE, Piscataway, NJ, USA, Dec. 12, 2010, pp. 165-166.

Annex to Form PCT/ISA/206 Communication Relating to Results of the Partial International Search, PCT/US2013, 028831, mailed May 17, 2013.

Finkel, J.R. et al., "Incorporating Non-local Information into Information Extraction Systems by Gibbs Sampling," Proceedings of the 43rd Annual Meeting of the Association for Computational Lingistics, Jun. 2005, pp. 363-370, Ann Arbor, Michigan, USA.

PCT International Search Report and Written Opinion, PCT Application No. PCT/US2013/028831, Oct. 10, 2013, sixteen pages.

Ratinov, L. et al., "Design Challenges and Misconceptions in Named Entity Recognition," Proceedings of the Thirteenth Conference on Computational Natural Language Learning, Jun. 2009, pp. 147-155, Boulder, Colorado, USA.

Ward, W., "Extracting Information in Spontaneous Speech," Proceedings of International Conference on Spoken Language Processing, Sep. 18-22, 1994, pp. 83-86, Yokohama, Japan.

Ward, W., "Understanding Spontaneous Speech: The Phoenix System," Proceedings of ICASSP '91, 1991, pp. 365-367.

Reithinger, "Robust Information Extraction in a Speech Translation System," Proceedings of EuroSpeech-99, pp. 2427-2430, 1999 (4 pages).

United States Office Action, U.S. Appl. No. 13/760,535, Apr. 28, 2015, 11 pages.

United States Advisory Action, U.S. Appl. No. 13/760,535, Aug. 20, 2015, 3 pages.

United States Office Action, U.S. Appl. No. 13/760,535, Dec. 3, 2014, 10 pages.

Australian First Examination Report, Australian Application No. 2013230453, Mar. 3, 2016, 2 pages.

Japanese Office Action, Japanese Application No. 2014-560989, Mar. 29, 2016, 8 pages.

Korea Intellectual Property Office, Office Action, Korean Patent Application No. 10-2014-7028069, Jun. 20, 2016, ten pages.

State Intellectual Property Office of the People's Republic of China, First Office Action, Chinese Patent Application No. 2013800203743, Jun. 2, 2016, twenty pages.

Canadian Office Action, Canadian Application No. 2,872,790, Sep. 23, 2016, 5 pages.

DEVICE FOR EXTRACTING INFORMATION FROM A DIALOG

PRIORITY CLAIM

This application is a continuation of U.S. application Ser. No. 13/760,535 filed Feb. 6, 2013, now allowed, which claims the benefit of, under 35 U.S.C. §119(e), U.S. provisional patent application Ser. No. 61/608,334, entitled "SPEECH TRANSLATION DEVICE WITH INFORMATION EXTRACTION," filed Mar. 8, 2012, all of which are incorporated herein by reference in their entirety.

BACKGROUND

Speech translation devices serve the purpose of bridging the language barrier between two (or more) human beings who do not understand each others language. This involves an arrangement where at least one speech translation system in at least one language direction is constructed from the combination of (1) a speech recognition engine, (2) a machine translation engine, and (3) an output generation interface that presents the output to the listener in the other language (such output may be presented by synthetic speech, output text on linked web clients, heads-up displays, projectors, special audio-speakers, etc.). The purpose of such a system is to provide human-to-human communication, i.e. to transmit ideas—information expressed by one speaker, to the listener in an other language. Prior patent references that disclose speech translation system include: U.S. Pat. Nos. 5,712,957; 6,324,510; 6,963,837; 8,090,570; 8,204,739; U.S. Pub. No. 2007/0271088; U.S. Pub. No. 2008/0120091; and U.S. Pub. No. 2011/0307241, all of which are incorporated herein by reference.

SUMMARY

There are many situations where the information transmitted in the process of a dialog is further used and processed in various information processing tasks. Currently, such information typically has to be entered, added or reentered into a different system of a human-machine interface, and is thus wasteful and time-consuming. The recognized dialog information, however, could also be exploited directly to a human-machine interface that "listens" to the human-human conversation. This application discloses in one general aspect an apparatus that becomes a component of a speech-translation device, and extends its capabilities to inform and direct various ancillary machine services, implicitly or explicitly, but as a side effect of the human-to-human communication. In so doing, it saves time, and renders information gathering more effective and efficient.

For example, in a speech translation device used in medical missions, two speakers (a doctor and a patient) might be discussing ailments that the patient might be experiencing. In the course of such a dialog, the doctor may ask questions, such as: "Do you have any fever", "any headache", or "do you have any allergies", that are all part of the diagnosis. Rather than entering the responses into a patient report or diagnosis and rather than writing down the resulting treatment, embodiments of the present invention can be used to generate such reports automatically, during the human-to-human dialog. Embodiments of the present invention can improve the effort of a knowledge worker by simplifying and unifying the work flow by extracting information as a side effect in a human-to-human dialog, or permit a rapid and efficient multimodal transfer or correction of such information during the human-human interaction.

In addition, the technique can be applied as a post-editing step based on a human-human interaction record. One important aspect of such a combined human-human and human-machine dialog is the treatment of errors. Not all information will be recognized and translated correctly, or subsequently correctly extracted and filled into the desired record. In such cases, human intervention may be necessary to verify and correct the resulting record. In certain embodiments, various multi-modal error repair techniques can be employed to correct the record.

In another general aspect, the present invention is directed to systems and method for resolving ambiguities occurring during speech translation of a human-to-human dialog between a first speaker speaking a first language and a second speaker speaking a second language. When an ambiguity is detected as part of either the speech recognition or translation processes, a disambiguation query is issued to the participants (e.g., the speakers). The disambiguation query is phrased so that a response resolves the ambiguity and permit the speech translation process to continue with higher confidence. A touch screen display may be used to issue disambiguation query and to receive a speaker's response.

FIGURES

Various embodiments of the present invention are described herein by way of example in conjunction with the following figures, wherein:

FIG. 8 is a flow chart of the process flow of the interactive disambiguation module according to various embodiments of the present invention;

DESCRIPTION

Figure 1:
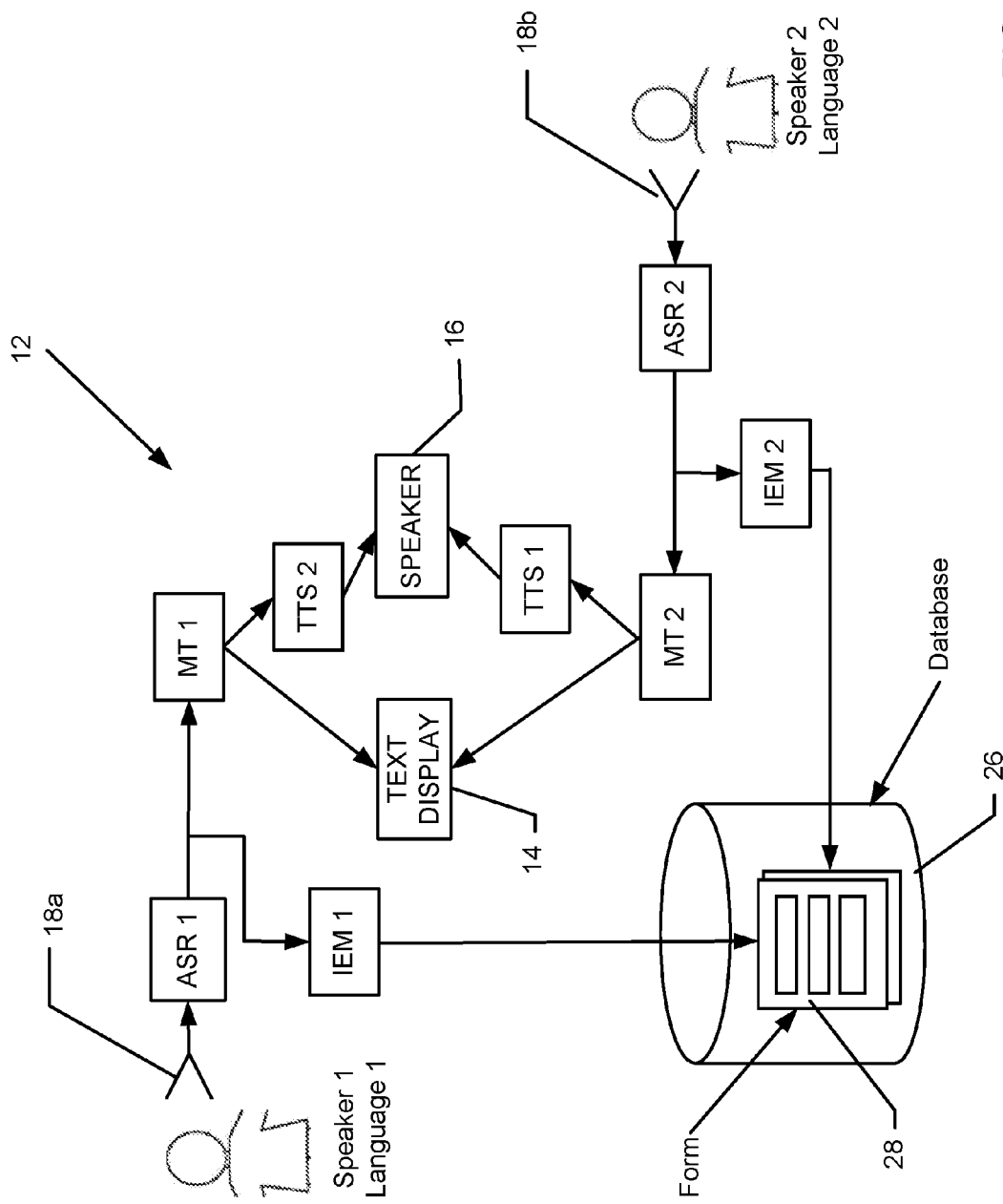
FIGS. 1-5 and 7 are diagrams of speech translation device according to various embodiments of the present invention.

FIG. 1 is a diagram of a speech translation device 12 with information extraction according to various embodiments of the present invention. The speech translation device 12 may operate in simultaneous translation mode, e.g., simultaneously translating speech from each of the two (or more) speakers. In FIG. 1, two speakers in two languages are shown (i.e., a 2-direction system), although the device could be expanded to handle multiple speakers (i.e., a multi-(3 or more) speaker system). In the embodiment of FIG. 1, input speech (or utterances) from Speaker 1 in Language 1 is input to an Automatic Speech Recognition engine (ASR 1) for Language 1. ASR 1 converts the input speech in Language 1 to text in Language 1 using, for example, conventional automatic speech recognition technologies. The text output from ASR 1 is input to Machine Translation engine (MT 1), which translates the text in Language 1 to Language 2. The translated speech in Language 2 from MT1 may be then output on a text display 14 (e.g., a computer monitor, a display on a smart phone or other portable computer, etc.)

and/or output in speech in Language 2 by a speaker 16 using a text-to-speech synthesizer (TTS 2) for Language 2.

Similarly, in the other direction, input speech from Speaker 2 in Language 2 is input to an Automatic Speech Recognition engine (ASR 2) for Language 2. ASR 2 converts the input speech in Language 2 to text in Language 2 using, for example, conventional automatic speech recognition technologies. The text output from ASR 2 is input to Machine Translation engine (MT 2), which translates the text in Language 2 to Language 1. The translated speech in Language 1 from MT2 may be then output on the text display 14 and/or output in speech in Language 1 by the speaker 16 using a text-to-speech synthesizer (TTS 1) for Language 1. Multiple additional arrangements in additional language directions may be added depending on application and deployment.

In addition, each direction includes an information extraction module, IEM 1 for Language 1 and IEM 2 for Language 2. IEM 1 receives the text output from the ASR 1 in Language 1 and IEM 2 receives the text output in Language 2 from the ASR 2. The IEMs are configured to extract relevant information from the human-to-human dialog.

Figure 6:
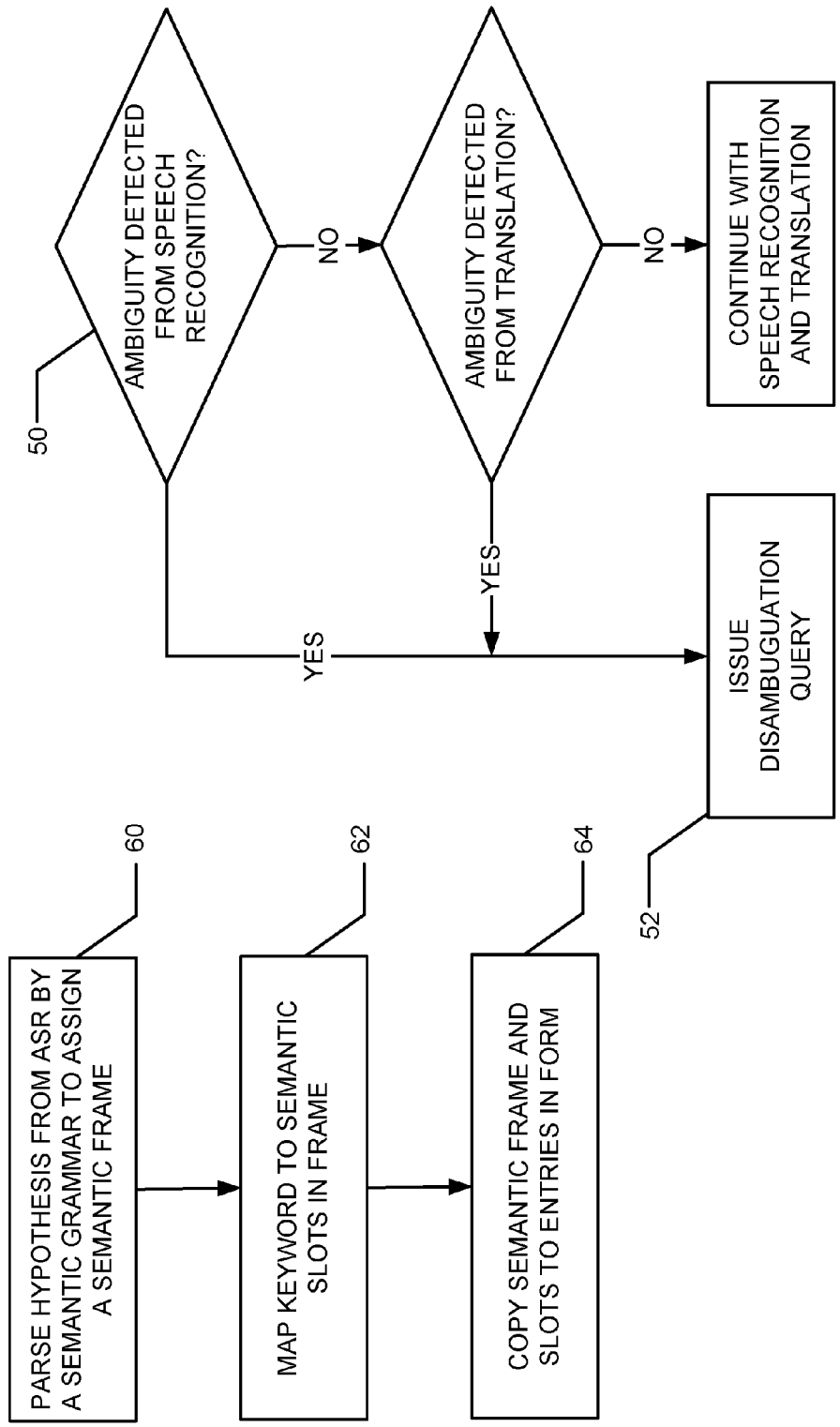
FIG. 6 is a diagram of the process flow information extraction module according to various embodiments of the present invention.

In one embodiment, the IEMs process their respective text inputs from the respective ASRs by formatting and parsing steps (PARS) to parse the textual sentence(s) from the ASR engines by a semantic grammar. In various embodiments, the IEMs may use a Phoenix parser to parse the text from the ASR engines. More details about Phoenix parsers may be found in W. Ward, "Extracting Information in Spontaneous Speech," *Proceedings of International Conference on Spoken Language*, 1994 and W. Ward, "Understanding Spontaneous Speech: the Phoenix System," *Proceedings of ICASSP* '91, 1991, both of which are incorporated herein by reference in their entirety. FIG. 6 is a flow chart illustrating the process flow of the IEMs according to various embodiments. At step 60, the parsing step may assign a semantic frame corresponding to the role or speech act of the spoken sentence and, at step 62, map a key word (or words) in that sentence to semantic slots in that frame. At step 64, the semantic frame and slots may then be copied into appropriate entries of an electronic form, where the form then constitutes the resulting report. The form 28 preferably is in either Language 1 or Language 2. Assuming for the same of discussion it is in Language 1, the form 28 is populated with recognized words from Speaker 1 in Language 1 and/or translated words from Speaker 2 that are translated from Language 2 to Language 1. The form may be an electronic form 28 stored in a data store of the speech translation system 12, such as a remote or local database 26, which database 26 may be stored in the primary or secondary memory of the speech translation system 12, or in a data store of a remote computer system. Depending on the speaker's role in the human-human interaction (e.g., doctor or patient), and depending on the grammars applied, the resulting form is then used as a diagnosis, treatment, or prescription, for example.

In another embodiment, instead of parsing, the IEMs use a spoken term detection or keyword spotting (KWS) module, which only extracts keywords instead of semantic frames, and copies them into the report. This keyword function might also be given by a named entity tagging module that identifies names in a text string. This is particularly useful where named entities (proper names, place names, medications, foods, etc.) are to be identified and filled in the form/report. Named entities play an important role in extracting names for requirements such as the preparation of patient records, hospital registration, refugee registration for disaster relief, and many more. More details about KWS modules may be found in L. Ratinov and D. Roth, "Design Challenges and Misconceptions in Named Entity Recognition," *CoNLL* (2009) and J. R. Finkel, T. Grenager, and C. Manning, "Incorporating Non-local Information into Information Extraction Systems by Gibbs Sampling," Proceedings of the 43rd Annual Meeting of the Association for Computational Linguistics (ACL 2005), pp. 363-370, which are incorporated herein by reference in their entirety.

Figure 2:
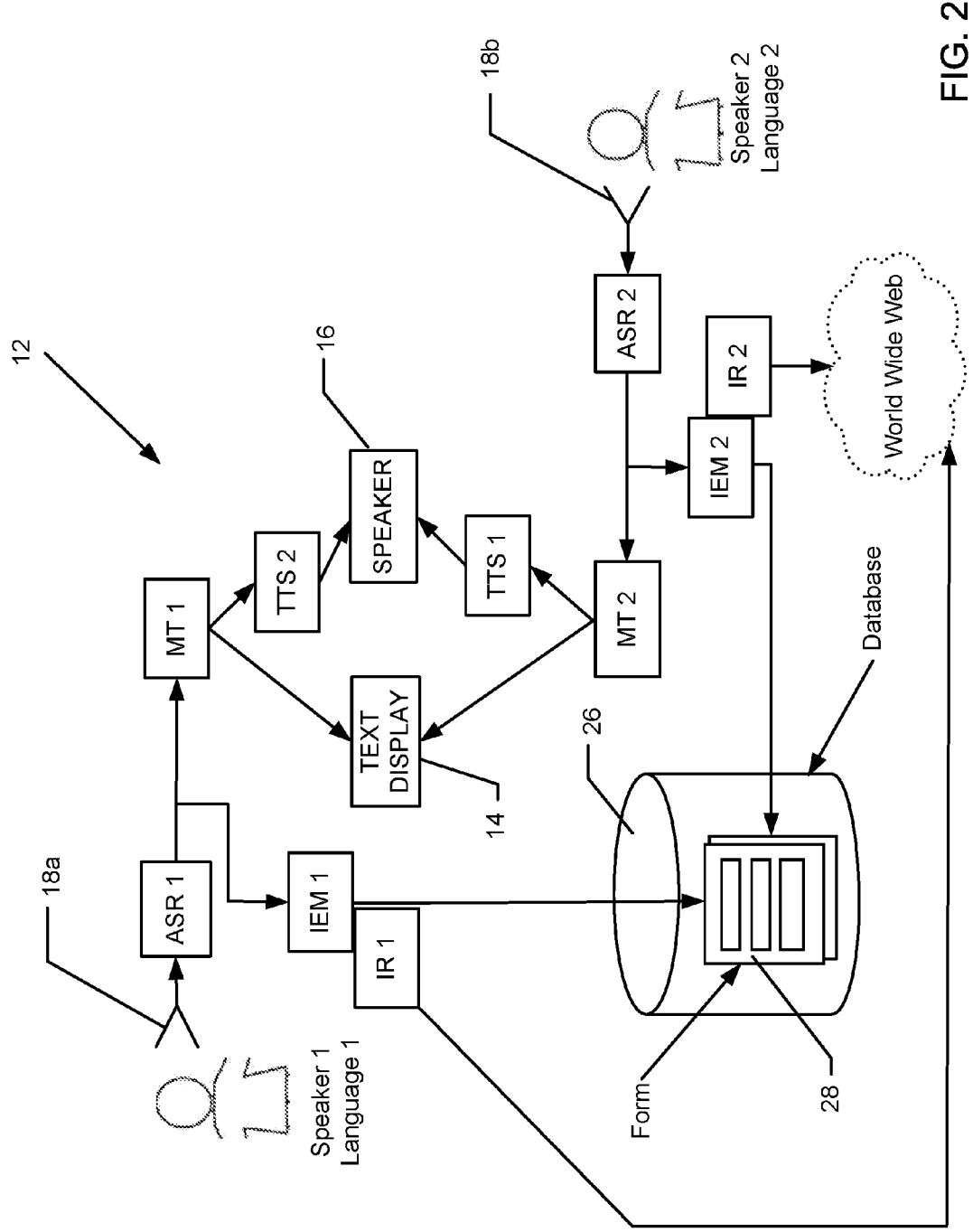

In another embodiment, the IEMs employ an information retrieval (IR) module. The IR modules IR1 and IR2 may extract relevant documents or responses from a large remote database of documents, including the World Wide Web, as shown in FIG. 2. The IEMs may be in communication with the World Wide Web via a wireless (e.g., WiFi) or wired network connection. In this manner, the IR modules IR1 and IR2 receive the transcribed input sentence and retrieve relevant documents that relate to it. The IR modules IR1 and IR2 may perform a search through large databases such as the World Wide Web, Wikipedia articles, Helpfiles, promotional material, product offerings, etc. to present the user (e.g., one of the speaker or another user) relevant articles, or instructions while they are conversing with another human. Possible applications are retrieval of instructions, relevant advertisement, entertainment, jokes, news, etc. depending on and as a side-effect of a human-human conversation. This embodiment is particularly well suited for less structured human-human dialogs, where the desired result is not a structure report, but relevant information.

The speech translation device 12 shown in FIGS. 1 and 2 may be implemented as a computer-based system with one or more processors that execute software code corresponding various modules (e.g., the ASR engines, the MT engines, the TTS units, and the IEMs). For example, as described further below in connection with FIG. 10, the random access memory (RAM) 212 and/or non-volatile data storage (e.g., ROM) 216 may store the software code for the ASR engines, the MT engines, the TTS units, and the IEMs, and the application processor 204 may execute the code. In one embodiment, the ASR engines, the MT engines, the TTS units, and the IEMs shown in FIGS. 1 and 2 could be implemented with a single computer-based device, such as a personal computer, a laptop, a tablet computer, a smart phone, etc. Although two microphones 18a, 18b are shown in FIGS. 1 and 2 (one for each speaker), the computer device could use one microphone for both (or more) speakers. The text output may be displayed the monitor/display of the computer device and/or output by a speaker. In some embodiments, a toggle input may be used to switch between the two (or more) speakers. In other embodiments, the speech translation device 12 may automatically identify the input language (e.g., Language 1 or Language 2) as described in U.S. published application Pub No. 2011/0307241. The database that stores the form/report, according to various embodiments, may be part of the memory of the computer device or in could be a remote database to which the data is uploaded via a computer-based, electronic phone and/or data network.

Figure 3:
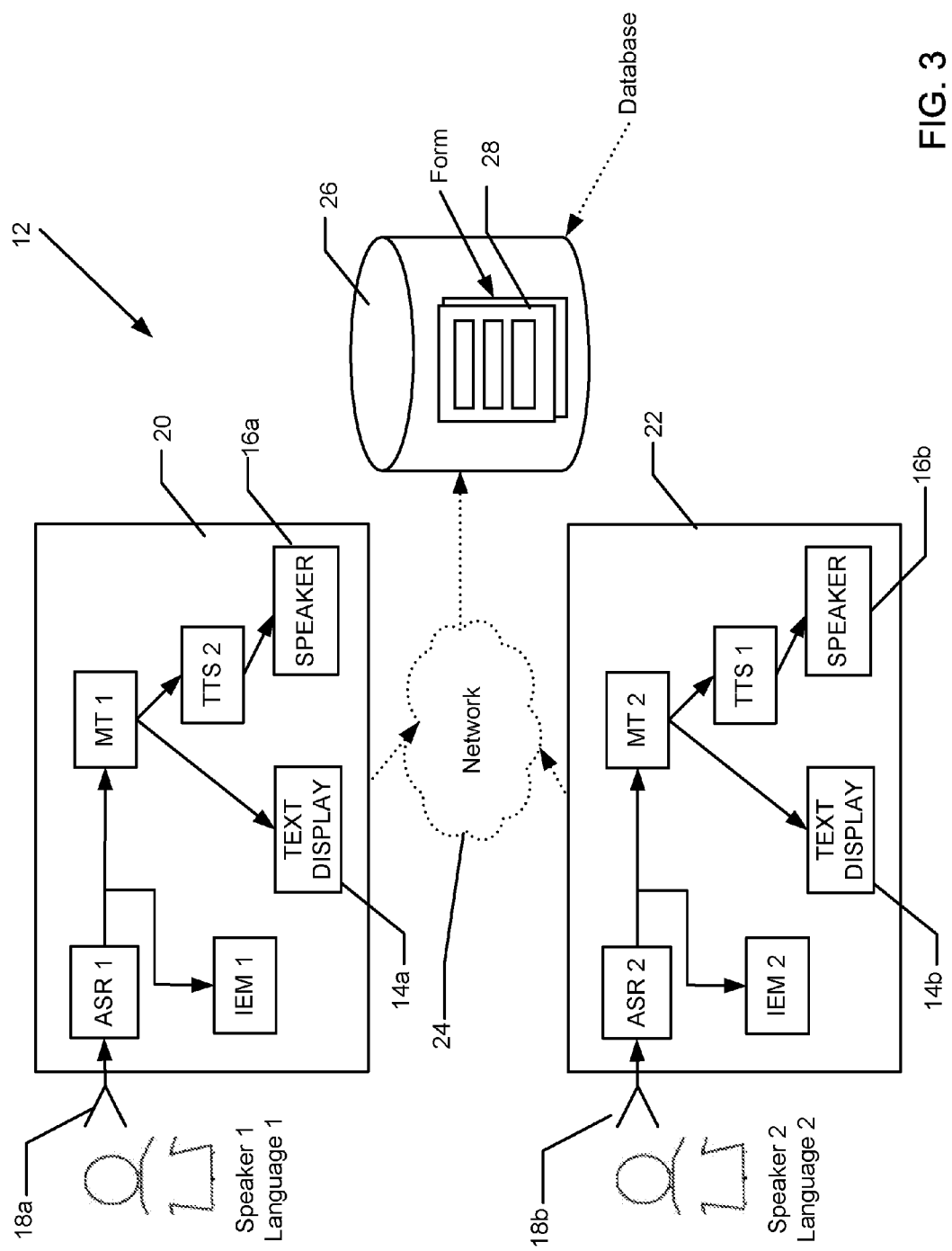

In other embodiments, a distributed computing system may be used. For example, as shown in FIG. 3, the components associated with Speaker 1 (e.g., ASR 1, MT 1, TTS 2, and IEM 1) could be on one computer 20 (e.g., smart phone, personal computer, laptop, etc.) and the components associated with Speaker 2 (e.g., ASR 2, MT 2, TTS 1, and IEM 2) could be on another computer device 22. The output from MT 1 may be transmitted to Speaker 2's computer device 22 via a computer-based, electronic phone and/or data network 24 and vice versa. In such embodiments, the database 26 may be in communication with the Speaker's computers via the phone and/or data network.

Figure 4:
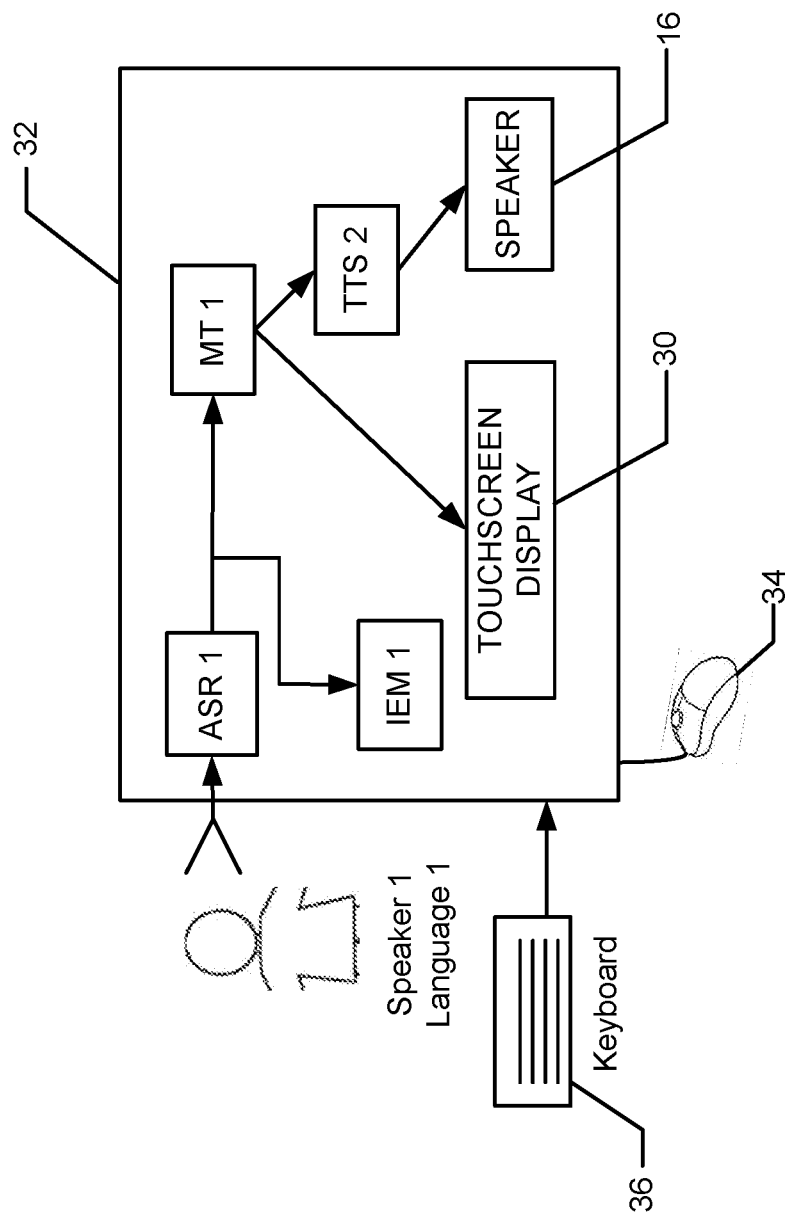

Various embodiments of the present invention can also be expanded by a multimodal interaction interface (MMII), as shown in FIG. 4. Speech recognition automatic spoken term detection or semantic parsing is far from perfect and will on occasion miss extracting relevant or important information. In order to make the reporting and retrieval function work robustly and efficiently, multimodal interaction can be used in various embodiments to identify key information by interactive means. The MMII may comprise one or more means by which a user can interact with the system to supply additional information to the system. For example, the display 30 of the speaker's computer device 32 may be a touch screen that detects the user's touch (by finger or stylus, for example) of the touch screen display 30. In such an embodiment, the text of the recognized speech from the speaker (Speaker 1) may be displayed on the display 30, and the speaker (Speaker 1) may identify a keyword in the displayed text by tapping on the appropriate keyword shown on the display 30. In other embodiments, the speaker (Speaker 1) could drag the keyword on the display 30 and drop it into the form (that is simultaneously displayed on the display 30) using the touch screen 30 and/or a conventional computer mouse 34 or keyboard 36. In addition, the user could correct an entry in the form (e.g., correct the spelling) by verbally inputting the correction (e.g., verbally providing the correct spelling for a term), which verbal input is detected by a microphone 38 of the device 32 and processed by speech recognition software (e.g., ASR1 and MT1) to correct the error in the form.

Transferring information from the human-to-human dialog to the forms should ideally always be done automatically, but multimodal interaction provides for a robust recovery mechanism from errors. In such a case, two different types of errors may be identified: omissions and erroneous information. In the case of omissions, the computer device (e.g., computer device 32 in FIG. 4) may have (and execute) software to provide multimodal support to enter the correct information. This includes dragging the correct information from the speech transcription to the form, and/or typing/spelling/handwriting the correct information into the form directly. In the case of errors, multimodal error correction techniques such as described in published U.S. application Pub. No. 2011/0307241, which is incorporated herein by reference in its entirety, may be used to correct the erroneous information. As mentioned above, the user could verbally input a correction. Also, the computer device 32 may have gesture recognition capabilities (e.g., a camera and video processing software) that can detect gestures or other movements of the user to indicate or correct an error in the form, or confirm the accuracy of the data in the form. In this manner, the user can handwrite, gesture, spell, respeak, paraphrase, etc. to correct the error and replace it by the correct information. For example, a simple dialog might be also be used to accomplish an error recovery by voice ("did you say John or Joan").

Figure 5:
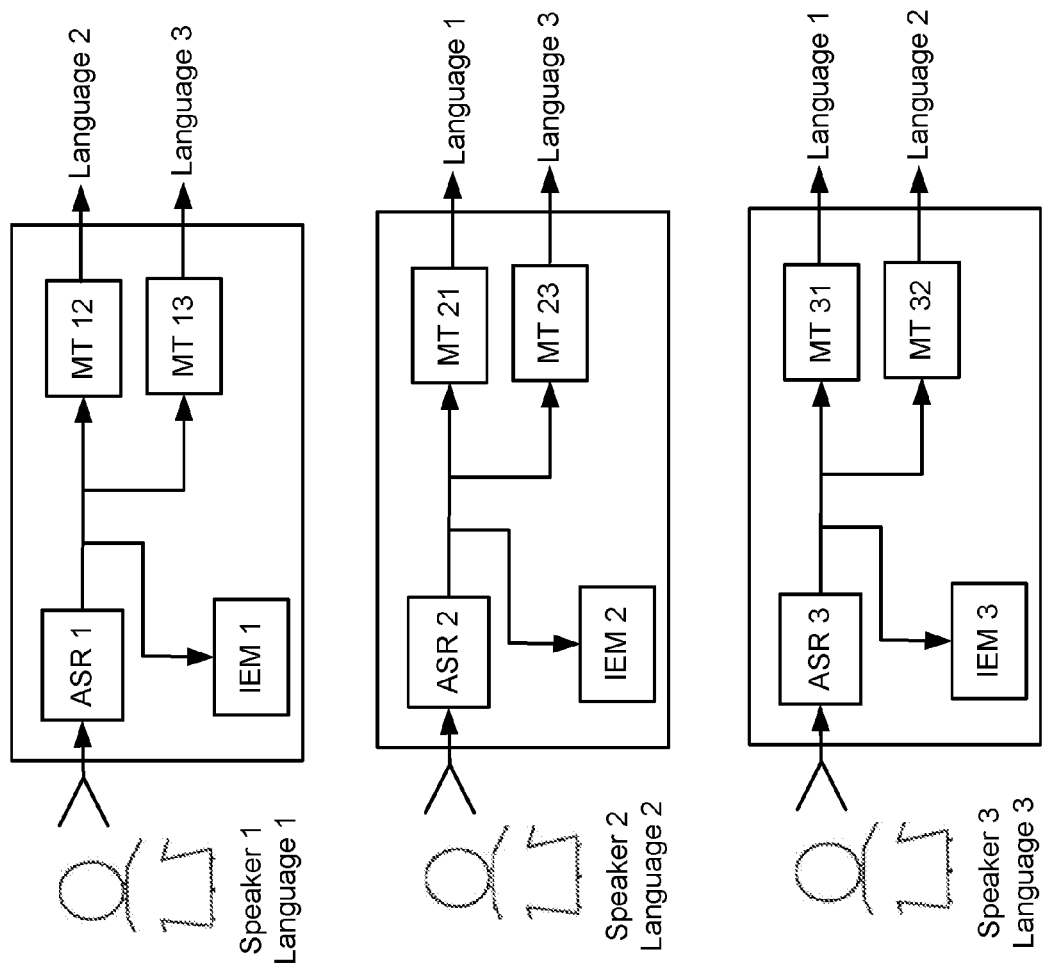

As mentioned above, the system could be used with multiple speakers. FIG. 5 shows such an embodiment with three speakers each speaking a different language. In this example with three speakers speaking Languages 1, 2 and 3 respectively, the utterances by Speaker 1 in Language 1 are translated into Languages 2 and 3; the utterances by Speaker 2 in Language 2 are translated into Languages 1 and 3; and the utterances by Speaker 3 in Language 3 are translated into Languages 1 and 2. The system could be extended in a similar manner to yet more speakers.

In various embodiments, the present invention can provide:

Implicit information extraction as a side effect to cross-lingual human-human dialogs.

Implicit information extraction as a side effect to monolingual human-human dialogs (as described further below).

Information extraction from human-human dialogs by application of a semantic parser.

Information extraction from human-human dialogs by application of a named entity tagger, word spotter or spoken term detection.

Information extraction from human-human dialogs by application of an information retrieval to find matching documents.

Application of the implicit information extraction extension in humanitarian and military deployments, refugee registration, registration, collection of statistics, disease outbreaks, doctor-patient dialogs, triage.

Application of implicit information extraction for advertising, humor, entertainment.

Multimodal form filling and correction. Correcting and completing missing entries by tactile (tapping), drag-and-drop; cross-modal spelling, handwriting, for correction or completion of missing information.

Layout of interface: Speech translation interface together with form to be filled on same screen.

Automatic filling (or pre-filling) of information in a form by information extraction. Cross-modal correction if pre-filling is not correct.

Provide alternative direct input, choice of implicit and explicit form filling. Different modalities, handwriting, clicking, respeaking, spelling as alternate direct inputs.

Sharing and uploading of report from speech translation interface.

Layout of interface: Speech translation interface together with form to be filled on same screen and favorites list.

Playback of instructions and preconfigured phrases in addition to speech translation, and form filling.

drag-and-drop, touch to transfer info from speech translation.

Prefill information automatically by information extraction. Cross-modal correction if prefill is not correct.

Provide alternative direct input, choice of implicit and explicit form filling. Different modalities, handwriting, clicking, respeaking, spelling as alternate direct inputs.

Provide error recovery by way of multimodal correction. Gesture to correct, and complementary modalities to replace errors by correct information.

Sharing and uploading of report from speech translation interface.

Provide mix of playback phrases, with free speech translation in addition to form filling.

Figure 9:
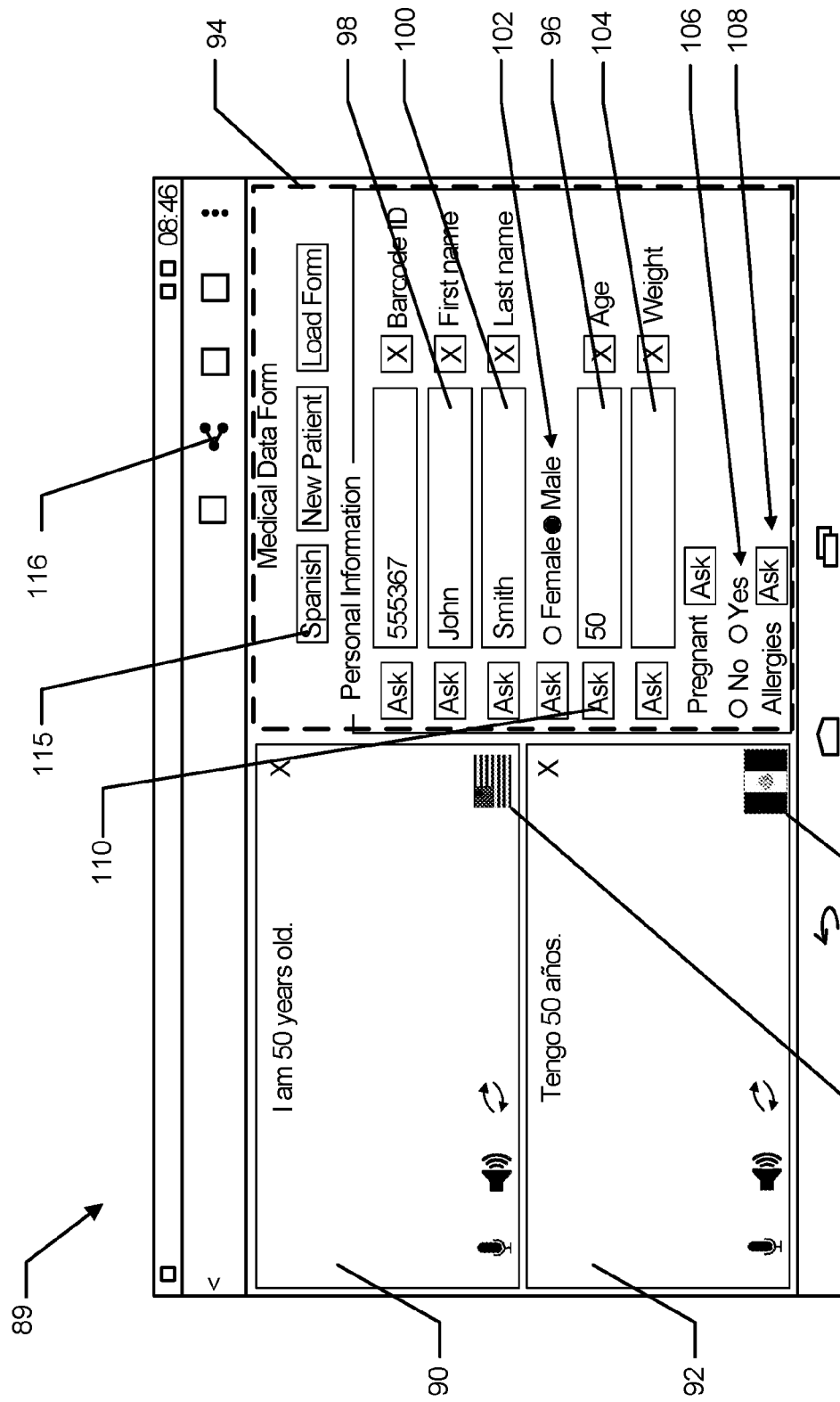
FIG. 9 is a diagram of a user interface for extracting information from a bi-lingual dialog according to various embodiments of the present invention.

FIG. 9 shows an example user interface 89 with a digital form that can be filled from extracting information in a human-to-human dialog. The form can be stored in a memory 26 of the device 12 and the interface 89, with the form 94, can be displayed on the display 14, for example. On the left are two fields 90, 92—one above the other in this example—that show the translated speech. This example assumes an English-Spanish translation scenario. If Speaker 1 is speaking English, the recognized speech from Speaker 1 in English is shown textually in field 90, and the Spanish translation is shown textually in field 92. Similarly, if Speaker 2 is speaking Spanish, the recognized speech from Speaker 2 is shown textually in field 92, and the English translation is shown textually in field 90. The fields 90, 92 may show the recognized speech and translations thereof of the two speakers in turn as the dialog between the two speakers progresses. In addition, the device speaker 16 may audibly output the translated speech so that the other speaker can hear it in their preferred language. For example, continuing with the same example as above where Speaker 1 is speaking English and Speaker 2 is speaking Spanish, the device speaker 16 may output the Spanish translation of Speaker 1's utterances for the benefit of Speaker 2, and conversely may output the English translation of Speaker 2's utterances for the benefit of Speaker 1. The user can select the desired first and second languages through the language selection input 91a-b.

Figure 10:
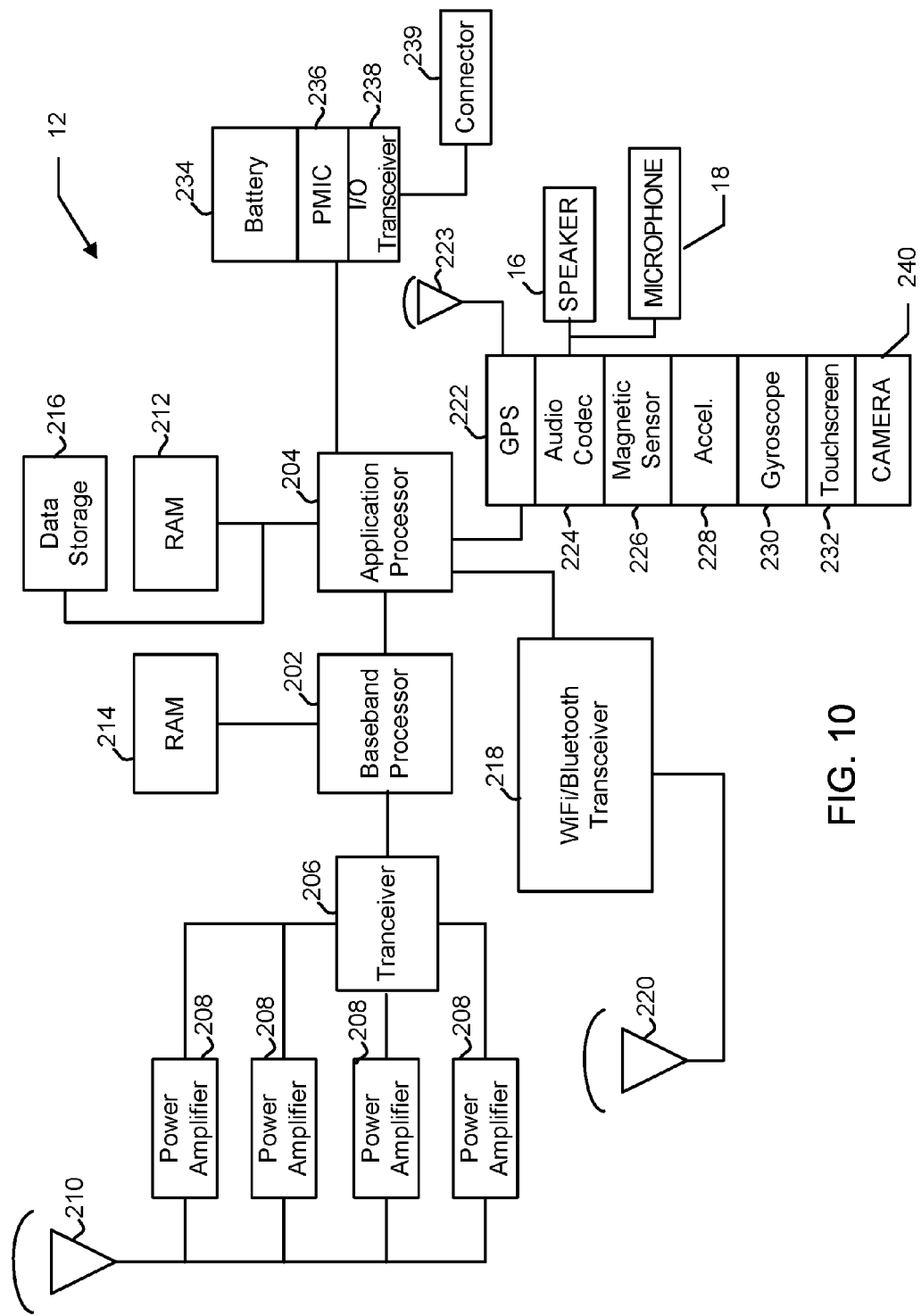
FIG. 10 is a block diagram of the speech translation device according to various embodiments of the present invention.

In the example of FIGS. 9-10, the form 94 to be populated through the human-human dialog is a medical data form. Such a form may be used, for example, in a doctor-patient dialog. As such, medical-related information is extracted from the dialog to fill in or populate the various fields of the form 94. The human-human (e.g., doctor-patient) dialog that is mediated by speech translation is shown in the fields 90, 92. Further, when key information (e.g., information relevant or applicable to the form 94) is presented in either language (i.e., English or Spanish in this example), it is extracted and prefilled in the applicable fields of the form 94. For example, the doctor may ask in Language 1 (e.g., English), "What is your age?" The patient may answer in Language 2 (e.g., Spanish) "Tengo 50 años" (which translates to "I am fifty years old" in English). The key information, here "50," can be extracted from the dialog and filled-in the age field 96 of the form. Moreover, the context of the question, e.g., "What is your age?," may be used by the device to ascertain that the patient's answer will include the age to be filled in the age field 96. In a similar manner, the doctor-patient dialog could be used to populate the other fields of the form, such as the name fields 98, 100, the sex field 102, the weight field 104, the pregnancy check field 106, the allergies field 108, etc.

In various embodiments, the form may also permit data entry by other modes besides speech extraction. For example, through a touch screen interface 14, for example, the user (e.g., the doctor) may click on the "male" and "female" fields in the form if the doctor is able to determine the sex of the patient without a question-answer dialog. Similarly, if the patient is male, the "not pregnant" response may be automatically populated.

In addition, in various embodiments, instead of Speaker 1 enunciating in Language 1 a question relevant to one of the fields of the form, e.g., asking in English "What is your age?," the user could activate (e.g., via the touch screen interface) an icon, e.g., "Ask" input 110, which when activated causes the device 12 to audibly output in the selected second language (Spanish in this example, see the language selection input 91) a prerecorded question designed to elicit the information for the associated field (e.g., the age field 96). For example, by activating the "Ask" input 100 associated with the age field 96, the device 12 may audibly output a question such as "¿Cuál es su edad?" ("What is your age" in Spanish) without the user having to first enunciate the question in Language 1 (e.g., English). Other fields in the form 94 could have associated "Ask" buttons that cause the device 12 to audibly output prerecorded questions designed to elicit the desired information for their associated field, as shown in the example of FIG. 9. The use of prerecorded questions can speed up the dialog by obviating the need for Speaker 1 (e.g., the doctor) to first enunciate the relevant question in Speaker 1's language. Moreover, the prerecorded questions for the "Ask" buttons can be adapted for the selected language to avoid confusion and ambiguity for Speaker 2 (e.g., the patient). That is, the prerecorded questions could be tested and proven to have little confusion and ambiguity in Language 2 to thereby increase the likelihood of an accurate response from Speaker 2, as well as accurate extraction by the device 12.

Similarly, in various embodiments, the interface 89 may provide buttons or inputs (not shown) where, when activated by the user, prerecorded instructional or explanatory information—as opposed to a question—is enunciated for Speaker 2 (e.g., the patient) in Language 2 (e.g., Spanish). Such prerecorded explanatory information can explain an aspect of the procedure to the patient, for example. For example, instead of the doctor (e.g., Speaker 1) saying in English, "I will now check your blood pressure" and then having the question translated into Language 2 (e.g., Spanish), the doctor could merely activate the associated tell button for blood pressure, in which case the device may audibly output "Ahora voy a revisar su presiön arterial" (Spanish for "I will now check your blood pressure"), thereby obviating the need for the doctor to first audiblize the explanation in Language 1 and then have it translated to Language 2. The prerecorded questions and explanations can save time and effort, particularly during repetitive queries such as patient's personal data (name, age, etc.) or the collection of vital signs.

In other embodiments, instead of having the questions and answers prerecorded, the device 12 may produce the questions and/or answers synthetically. For example, the user could generate his/her own questions or explanations in Language 1 for various fields of the form 94, being input and stored in the device 12 via speech or text, for example. The device 12 can translate this input as explained above into Language 2 when needed.

Of course, FIG. 9 is but one example of a medical data form and different forms, with different and/or additional data fields, could be used. Also, other uses besides a medical data forms could be used.

It should be noted that not always will the extraction of the information from the human-human dialog be accurate or correct. The device 12 in various embodiments may provide means for repairing or correcting the information in the form. These means can be other than speech extraction, i.e., other input modes (e.g., allowing multi-modal input for the form). For example, using the touch screen interface 14, the user (e.g., Speaker 1) could drag information from either of the fields 90, 92 to appropriate field in the form 94 by a touch and drag gesture or input.

Alternatively or additionally, in other embodiments different modes of form correction or data entry can be used. For example, in various embodiments the user (e.g., the doctor) could click on or otherwise selected extracted data in the form 94 to edit the data in the form. For example, in various embodiments the user could edit (or delete) the selected data via a keyboard (including a touch screen keyboard), by respeaking the data for speech extraction, by a handwriting gesture on the touch screen interface 14, or by any other suitable means. Similarly, the information can be entered independently without explicitly asking a question related to the form 94, as mentioned above. For example, the doctor may see that the patient is female, and just click or type the information on the form 94 directly, thus bypassing the human-human dialog altogether at this stage. In this case, the user (e.g., Speaker 1) may choose to push on the field directly and activate speech recognition in either language to enter the information directly. Alternatively, the information for the field in the form 94 may be typed or spelled or handwritten. U.S. Pat. Nos. 5,712,957 and 5,855,000, which are incorporated herein by reference in their entirety, provide details on various multi-modal correction techniques.

FIG. 10 is a block diagram of a device 12 according to various embodiments of the present invention. In such an embodiment, the device 12 may be implemented as a smart, portable device, such as a laptop computer, a smart phone, or a tablet computer, for example. As shown in the example of FIG. 10, the device 12 may comprise multiple processors 202, 204. A baseband processor 202 may handle communication over a mobile telecommunications network (e.g., cellular network) according to any suitable communications technology (e.g., 3G, 4G, etc.). The baseband processor 202 may comprise dedicated random access memory (RAM) 214. In various embodiments, the baseband processor 202 may be in communication with a transceiver 206. The transceiver 206 may, subsequently, be in communications with one or more power amplifiers 208 and an antenna 210. Outgoing signals for the mobile telecommunications network may be processed at baseband by the baseband processor 202 and provided to the transceiver 206. The transceiver 206 and/or the baseband processor 206 may modulate the outgoing signal to a carrier frequency. One or more of the amplifiers 208 may amplify the outgoing signal, which may be subsequently transmitted via antenna 210. Incoming signals for the mobile telecommunications network may be received by the antenna 210, amplified by one or more of the amplifiers 208 and provided to the transceiver 206. Either the transceiver 206 or the baseband processor 202 may demodulate the incoming signal to baseband.

An applications processor 204 may execute an operating system as well as software applications, including the speech recognition and translation modules described herein (e.g., the ASR, MT, TTS and IEM modules shown in FIG. 1). The applications processor 204 may also execute the software for the touch screen interface 232, including the techniques for inputting and correcting data shown on the form 94 displayed on the touch screen interface 232. The applications processor 204 may also be in communications with applications RAM 212, and non-volatile data storage (e.g., ROM) 216. The applications processor 204 may additionally be in communication with other hardware devices such as a combination WI-FI/BLUETOOTH transceiver 218. The WI-FI/BLUETOOTH transceiver 218 may handle radio frequency (RF) communication with a LAN (e.g., according to the WI-FI standard, or any suitable standard) or direct RF communications between the device 200 and another wireless device (e.g., according to the BLUETOOTH standard or any suitable standard). In various embodiments, the device 200 may also comprise a global positioning system (GPS) 222 that is in communication with a satellite-based GPS system via a GPS antenna 223 for providing the application processor 204 information describing the geographic location of the device 200. The touch screen 232 may both provide output to the user of the device 12 in visual form and receive input from the user. The input may be in the form of signals representing screen-touches by the user. An audio codec module 224 may provide hardware and/or software for decoding and playing audio signals. In some embodiments, the codec 224 may also comprise a digital-to-analog converter. Audio output signals may be provided to the device speaker 16 and/or a jack (not shown) that may receive a set of headphones and/or speakers for playing the audio output signal. Audio input signals may be provided via the device microphone(s) 18. The device may also comprise a digital camera 240.

Various other sensors may be included in certain embodiments. A magnetic sensor 226 may sense magnetic fields near the device. For example, the magnetic sensor 226 may be used by various apps and/or system functionality to implement a compass. An accelerometer 228 and gyroscope 230 may provide data describing movement of the device. For example, data from the accelerometer 228 and gyroscope 230 may be used to orient the display of the touch screen 232 (e.g., portrait versus landscape). The device 200 may be powered by a battery 234, which may, in turn, be managed by a power management integrated circuit (PMIC) 236. An I/O transceiver 238 may manage wired communications between the device and other devices, for example, according to the Universal Serial Bus (USB) or any other suitable standard. A connector 239 may facilitate wired connections. In some embodiments, connections via the connector 239 and I/O transceiver 238 may provide power for charging the battery 234.

Returning to the example form in FIG. 9, to add or confirm the extracted information, other data entry modalities can be used, such as GPS information (via the GPS receiver 222), camera input (via the camera 240), accelerometers 228, bar code readers (via a bar code app running on the device or a separate hardware barcode reader that is part of the device, for example), etc., to derive information such as gender or person identification, location, etc. This may complement the speech dialog to fill in information automatically, and thus improve efficiency. The complementary information, may also improve accuracy of the extracted information or cross-validate given information. For example, automatic gender classification from speech may prefill the gender field 102 along with the doctor's comment or clicks. Or the name may be verified by a camera face identification or speaker identification, or a bar code read.

In various embodiments, questionable information may be determined by way of confidence measures that use both acoustic confidences, as well as complementary information that confirms plausibility of the extracted information. The questionable information in the form may be called out, for example, such as by highlighting. For example, a doctor may enter the gender of the patient directly, but confidence measures may highlight the information if acoustic confidences and speaker/gender ID suggest that the information could be in error. Low confidence information may be highlighted or otherwise called out in the form as well as in the text of the speech translation dialog window. Other sources of low confidence may be derived from the detection of Out-of-Vocabulary (OOV) items, acoustic, semantic and translation ambiguities. Low confidence regions may be highlighted and the ambiguity explained (similar word, alternate meaning, missing word, etc.).

In the example of FIG. 9, the form 94 is completed in English. The user of the device 12 could toggle back and forth between Language 1 (e.g., English) and Language 2 (e.g., Spanish) by activating the form language input 115. When activating the input 115, the form 94 may transition from being displayed in Language 1 (English in this example) to Language 2 (Spanish in this example), and vice versa upon a second activation of the input 115, and so on. In this manner, Speaker 1 (e.g., doctor) could view the form in Language 1 (e.g., English), and then transition the form to Language 2 (e.g., Spanish) for confirmation and/or verification by Speaker 2 (e.g., the patient).

In addition, in various embodiments, the speech translation device 12 permits the definition of the forms themselves. For example, the form(s) may be read in from a template form (e.g., a spreadsheet such as Excel) and generate a form (as shown in the example of FIG. 9). A practitioner (such as in our example, the doctor) can edit the template forms as needed to add questions or comments, then read a new form in. The speech translation may then automatically generate translations for each form label, form messages, and later the extracted information.

Additionally, via the transceiver 206 or the transceiver 218, the device 12 may be able to share a form (stored in database 26), completed or not, by email or electronic patient record upload, for example, thereby enabling incremental and instantaneous updates of information records at centralized databases from mobile portable devices. In various embodiments, the user may initiate such wireless transmission or uploading of the form by activating the share icon 116. The uploaded/transmitted form may or may not include the actual dialog data as well as pertinent multimodal user interaction, queries and edits, thus providing granular information on the entire human-human encounter and interaction.

In various embodiments, the device may operate (e.g., translate speech and extract the form-fillable information) in simultaneous and consecutive translation mode. In simultaneous mode, the device uses the transcript and translation of an ongoing continuous dialog in real-time without the use of push buttons or other inputs to toggle between speakers, and without waiting for the translation to complete. In this case, the device extracts the relevant and pertinent information into the forms as above and error correction works the same. In consecutive translation mode, the speakers take turns speaking and speak consecutively. They may use a button or other input on the device (such as on the touch screen interface 14) to transition from one translation channel (e.g., translation from Language 1 to Language 2) to the other (e.g., translation from Language 2 to Language 1). The interface may selectively enable or disable the speech translation and/or the form windows for the convenience of the user.

Figure 7:
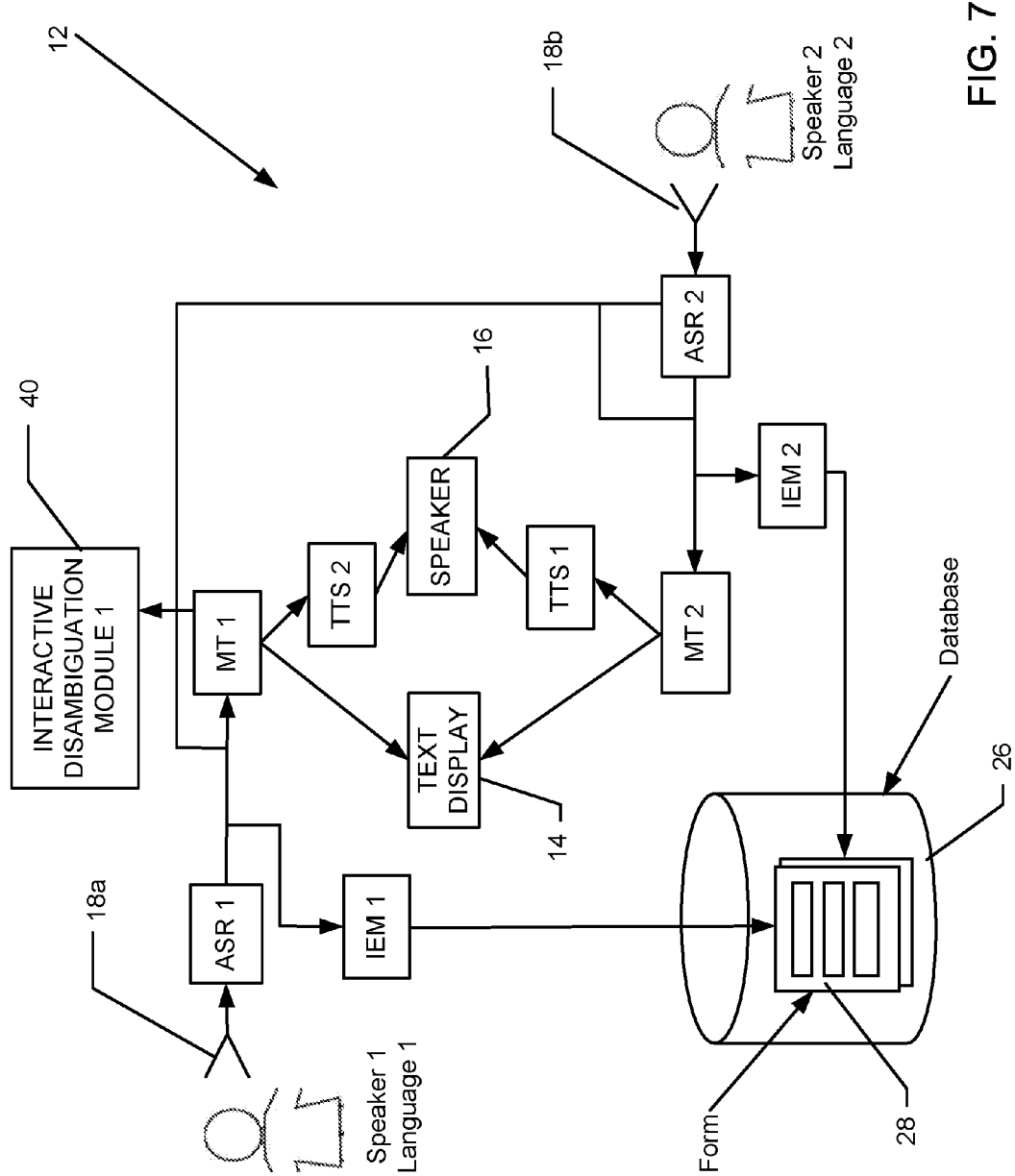

In addition, as shown in the example of FIG. 7, in various embodiments the device may include and execute software for interactive disambiguation, for example, the interactive disambiguation module 40, whereby the device 12, using the interactive disambiguation module 40, assumes initiative and proposes feedback on possible errors and near misses if ambiguities or errors are suspected. In various embodiments, this may to occur at two levels: the recognition and the translation level. On the recognition level, if the recognition (determined by the ASR modules 1 or 2, as the case may be) is of low confidence, or if the recognized text is in conflict or in mismatch to what would be expected at the level of the form, the interactive disambiguation modules 40 may issue a query back to the user, such as audibly via an internal speaker 16 and/or visually via the text display 14. As too many disambiguation queries would annoy the user, the time and moment to ask for clarification should preferably is chosen carefully. In various embodiments, several criteria to assess the confidence or plausibility of a recognition hypothesis may be used:

Acoustic confidence score that establishes if the acoustic signal is likely to be the sentence that was recognized.
Plausibility in the context of the form to be filled or information to be extracted. A recognition of "We met on Tuesday" may be more likely than "We met and who's he?" if the speaker are currently discussing dates of the week at the level of the form that is to be filled. Thus, if ambiguous words exist that fit with common options in the form (e.g., "Tuesday"), the recognition hypothesis "We met and who's he" should be questioned.
Language context given by the translation from the utterances of the other speakers (in their language) can also condition the expectation and thus question or alter a recognition hypothesis. In the example above, if the other speaker said in Spanish "cuando se han encontrado", the translation of this sentence into English "When did you meet" provides language modeling context that would raise the likelihood of the hypothesis "Tuesday" over "Who's he?".

The three confidence measures may be used to decide when to request a disambiguation from the user. In various embodiments, one or more of these criteria are combined in one confidence or clarification score. A disambiguation query may then be issued to solicit clarification.

At the translation level, the of the interactive disambiguation module 40 may request disambiguation based on input from the MT engine (e.g., MT1 or 2) in various embodiments if (a) several output translations are possible and of similar likelihood (there is at least one other translation that is within a threshold scoring difference of the highest scoring translation), or if (b) there is one more likely output (e.g., there are no alternative output translations within the threshold scoring difference from a highest scoring output translation), the highest scoring output has a low confidence in the target language and is likely to be wrong. In the later case (b), a query back to the user in his/her (source) language may be issued, alerting the speaker of the likely problem and requesting a restatement or a paraphrase for clarity. In the former case (a), two or more alternatives need to be considered. In this case, the system may present to the user these two cases embedded in a carrier sentence in the source language that disambiguates the two uses of the work in the target language. For example, if the user speaks the following sentence in English—"This is my nail"—the word "nail" may be considered ambiguous and may be translated in Spanish as "clavo" or as "uña". If the translation probabilities of both outcomes are comparable within a threshold of plausibility, the system can request disambiguation from the user. In various embodiments, this may be then done by searching for phrases that contain the word in question in either of its usage in a training database. For example, the speaker's devices may be connected via a data network to a remote computer system that search a remote training database. The remote computer system may detect the disambiguation or one of the speaker's devices may detect the disambiguation. In alternative embodiments, instead of a training database a traditional dictionary could be used, which could be stored on the speaker's device or remotely.

On the source side, the system is then in a position to ask the user: "did you mean nail as in: "they used nails to fix the door", or as in "she painted her nails red". If the user then selects one or the other solution, the system will adopt the selected translation meaning, and increase the translation probabilities for this word. Presentation of the two ambiguous options can be given graphically on the display or by a verbal disambiguation phrase.

The code for the disambiguation module may be stored in the RAM 212 and/or non-volatile data storage 216, and may be executed by the application processor 204, for example. See FIG. 10.

FIG. 8 is a flow chart of the process flow of the interactive disambiguation module 40 according to various embodiments. In this example, assume Speaker 1 is speaking in Language 1, which is to be translated to Language 2 for the benefit of Speaker 2. At step 50 the interactive disambiguation module 40 determines whether there is an ambiguity in the recognized speech in Language 1 of Speaker 1. As described above, the interactive disambiguation module 40 may make this determination based on (i) the acoustic recognition confidence level score from the ASR1 for the utterance by Speaker 1, (ii) the plausibility of the hypothesis of ASR1 based on the information to be extracted (e.g., the form to be filled), and (iii) the plausibility of the hypothesis based on the language context of the translation from the utterances by the other speaker (e.g., Speaker 2, from MT2). Based on these scores and assessments (and possibly others), the interactive disambiguation module 40 determines whether a disambiguation query should be issued to Speaker 1. If so, at step 52 the disambiguation query is issued, such as described above.

If not ambiguity is detected as step 50, the process flows to step 54, where it is determined whether a disambiguation query is necessary based on the translated speech of Speaker 1 from Language 1 to Language 2. This may be done as described previously. If a disambiguation query is needed, the process flows to step 52 where the disambiguation query is issued. Of course, if no disambiguation query is needed due to translation either, the system continues with the normal speech recognition and translation process at step 56. As mentioned above, the disambiguation queries at step 52 may have different formats based on the type of ambiguity, e.g., recognition versus translation.

The above-described disambiguation capability can be used with or without the information extraction capability according to various embodiments.

In the above description, the information extraction process was described in the context of a bi-lingual dialog. In other embodiments, the information extraction process could be performed in the process of a mono-lingual dialog. Similar to the bi-lingual mode, the device in the mono-lingual mode may perform speech recognition on the speech utterances by the speakers and extract key information in the recognized speech to fill in the various and applicable fields of the form 28. Using the same example as above from the bi-lingual mode, the doctor may ask in the first language (e.g., English) "What is your age?" The patient may answer in the same language (i.e., a mono-lingual dialog) "I am fifty years old." The key information, here "50," can be extracted from the dialog and filled-in the age field 96 of the form 94 (see FIG. 9). Moreover, the context of the question, e.g., "What is your age?," may be used by the device to ascertain that the patient's answer will include the age to be filled in the age field 96. In a similar manner, the doctor-patient dialog could be used to populate the other fields of the form, such as the name fields 98, 100, the sex field 102, the weight field 104, the pregnancy check field 106, the allergies field 108, etc. Referring to the example interface of FIG. 9, in such an embodiment, text of the recognized speech of the two speakers in the common language (e.g., English) may be displayed respectively in the two fields 90, 92. Extracted information from the mono-lingual dialog between the two speakers may be displayed in the form 94 on the right.

In addition, as before, the device 12 may be able to share the form, completed or not, by email or electronic patient record upload, thereby enabling incremental and instantaneous updates of information records at centralized databases from mobile portable devices. The uploaded/transmitted form may or may not include the actual dialog data as well as pertinent multimodal user interaction, queries and edits, thus providing granular information on the entire human-human encounter and interaction Accordingly, pursuant to various embodiments, the present invention is directed to a device for extracting information from a human-to-human dialog between at least a first speaker and a second speaker. The device may comprise at least one microphone, a screen display, at least one programmable processor and at least one data storage unit for storing digital data. The at least one programmable processor is in communication with the at least one microphone and the screen display. Further, the at least one programmable processor is programmed to: (i) automatically recognize speech by the first speaker received by the at least one microphone; (ii) automatically recognize speech by the second speaker received by the at least one microphone; (iii) extract at least information from the recognized speech by the second speaker; and (iv) enter the extracted information from the recognized speech by the second speaker into an electronic form that is stored in the at least one data storage unit of the computer system and displayed in a graphical user interface on the screen display.

According to various implementations: the first speaker speaks a first language;
the second speaker speaks a second language that is different from the first language; and
the at least one programmable processor is further programmed to: (i) automatically translate the recognized speech by first speaker in the first language to the second language; (ii) automatically translate the recognized speech by second speaker in the second language to the first language; (iii) extract at least information from the recognized speech by the second speaker by extracting at least information from the translation of the recognized speech by the second speaker translated to the first language; and (iv) enter the extracted information by entering the extracted information from the translation of the recognized speech by the second speaker translated to the first language into the electronic form stored in the at least one data storage unit. In addition, the processor may be further programmed to: (v) extract at least information from the recognized speech by the first speaker in the first language; and (vi) enter the extracted information from the recognized speech by the first speaker in the first language into the electronic form.

According to various implementations, the processor is programmed to extract the information from the translation of the recognized speech by the second speaker translated to the first language by parsing the translation by a semantic grammar. In addition, the processor may be further programmed to retrieve one or more documents related to the extract information from a remote database. In addition, the processor is programmed to extract the information from the translation of the recognized speech by the second speaker translated to the first language by detecting one or more keywords in the translation. Additionally, the processor may be further programmed to solicit feedback from at least one of the first speaker and the second speaker prior to entering the extracted information in the electronic form. Also, the at least one programmable processor may be programmed to recognize and received an edit to extracted information in the electronic form input via the screen display by a user of the device.

In another general aspect, the present invention is directed to a computer-based device for extracting information from a human-to-human dialog between at least a first speaker and a second speaker. The device comprises at least one microphone, a screen display, and at least one data storage unit for storing digital data. The device also includes a first automatic speech recognition module for automatically recognizing speech by the first speaker received by the at least one microphone. The device further includes a second automatic speech recognition module for automatically recognizing speech by the second speaker received by the at least one microphone. In addition, the device includes an information extraction module in communication with the first and second automatic speech recognition modules, the at least one microphone and the screen display. The information extraction module is for: (i) extracting at least information from the recognized speech by the second speaker; and (ii) entering the extracted information from recognized speech by the second speaker into an electronic form that is stored in the at least one data storage unit and displayed on a graphical user interface on the screen display.

According to various implementations: the first speaker speaks a first language; the second speaker speaks a second language that is different from the first language; and the device further comprises: (i) a first machine translation module in communication with the first automatic speech recognition module, wherein the first machine translation module is for automatically translating the recognized speech by first speaker in the first language to the second language; and (ii) a second machine translation module in communication with the second automatic speech recognition module, wherein the second machine translation module is for automatically translating the recognized speech by second speaker in the second language to the first language. In such an implementation, the information extraction module is for: (i) extracting at least information from the recognized speech by the second speaker by extracting at least information from the translation of the recognized speech by the second speaker translated into the first language; and (ii) entering the extracted information by entering the extracted information from translation of the recognized speech by the second speaker translated to the first language into the electronic form stored in the at least one data storage unit.

In various implementations, the information extraction module is further for:
(i) extracting at least information from the recognized speech by the first speaker in the first language; and (ii) entering the extracted information from the recognized speech by the first speaker in the first language into the electronic form. The information extraction module may extract the information from the translation of the recognized speech by the second speaker translated to the first language by parsing the translation by a semantic grammar. Also, the device may comprise an information retriever module for retrieving one or more documents related to the extract information from a remote database. In addition, the information extraction module may extract the information from the translation of the recognized speech by the second speaker translated to the first language by detecting one or more keywords in the translation. The device may further comprise a multimodal interaction interface to solicit feedback from at least one of the first speaker and the second speaker prior to entering of the extracted information in the electronic form.

In yet another general aspect, the present invention is directed to a computer-implemented method for extracting information during a human-to-human dialog between at least a first speaker and a second speaker speaking. The method may comprise the steps of:

(i) receiving, by at least one microphone of a computer-based information extraction device, speech by the first and second speakers during the dialog; (ii) automatically recognizing, by the computer-based information extraction device, the speech by the first speaker; (iii) automatically recognizing, by the computer-based information extraction device, the speech by the second speaker in the second language; (iv) extracting, by the computer-based information extraction device, at least information from the recognized speech by the second speaker; and (v) entering, by the computer-based information extraction device, the extracted information from the recognized speech by the second speaker into an electronic form stored in at least one data storage unit of the information extraction device.

In various implementations, the method may further comprise the step of displaying the form on a screen display of the computer-based information extraction device. Also, in a situation where the first speaker speaks a first language and the second speaker speaks a second language that is different from the first language, and the method may further comprise the steps of: (i) automatically translating, by the computer-based information extraction device, the recognized speech by first speaker in the first language to the second language; (ii) and automatically translating, by the computer-based information extraction device, the recognized speech by second speaker in the second language to the first language. Also, the step of extracting at least information may comprise extracting by the computer-based information extraction device at least information from the translation of the recognized speech by the second speaker translated to the first language. And the step of entering the extracted information may comprise entering, by the computer-based information extraction device, the extracted information from the translation of the recognized speech by the second speaker translated to the first language into the electronic form stored in the at least one data storage unit of the information extraction device In various implementations, the method further comprises: extracting at least information from the recognized speech by the first speaker in the first language; and entering the extracted information from the recognized speech by the first speaker in the first language into the electronic form. Extracting the information from the translation of the recognized speech by the second speaker translated to the first language may comprise parsing the translation by a semantic grammar. The method may further comprise retrieving, by the computer-based information extraction device, one or more documents related to the extract information from a remote database. Extracting the information from the translation of the recognized speech by the second speaker translated to the first language may comprise detecting one or more keywords in the translation. The method may also further comprise the step of soliciting, by the computer-based information extraction device, feedback from at least one of the first speaker and the second speaker prior to entering the extracted information in the electronic form. In addition, the method may further comprise: (i) determining, by the computer-based information extraction device, whether there exists an ambiguity in the recognized speech of the first speaker; (ii) determining, by the computer-based information extraction device, whether there exists an ambiguity in the translation of the recognized speech of the first speaker in the first language into the second language; and (iii) upon a determination by the computer-based information extraction device that there is ambiguity in either (a) the recognized speech of the first speaker or (b) the translation of the recognized speech of the first speaker in the first language into the second language, issuing by the computer-based information extraction device a disambiguation query to the first speaker via the screen display of the computer-based information extraction device, wherein a response to the disambiguation query resolves the ambiguity. The disambiguation query issued to the first speaker may be different when the ambiguity is in the recognized speech of the first speaker than when the ambiguity is in the translation of the recognized speech of the first speaker in the first language into the second language. Also, the determination of whether there exists an ambiguity in the recognized speech of the first speaker may be based upon a plurality of factors, including: (i) an acoustic confidence score in the recognized speech of the first speaker; (ii) a context of the electronic form; and (iii) a language context given by a translation of one or more utterances from the second speaker from the second language to the first language. Determination of whether there exists an ambiguity in the translation of the recognized speech of the first speaker in the first language into the second language also may be based upon a plurality of factors, including: whether there are one or more alternative output translations within a threshold scoring difference of a highest scoring output translation; and whether, if there are no alternative output translations within the threshold scoring difference of the highest scoring output translation, the score for the highest scoring output translation is below a minimum threshold.

In yet another general aspect, the present invention is directed to a computer-implemented method of resolving ambiguity in a speech translation of a human-to-human dialog between at least a first speaker speaking a first language and a second speaker speaking a second language. The method may comprise the steps of: (i) recognizing, by a computer-based speech translation system, speech by the first speaker in the first language; (ii) determining, by the computer-based speech translation system, whether there exists an ambiguity in the recognized speech of the first speaker; (iii) translating, by the computer-based speech translation system, the recognized speech of the first speaker in the first language into the second language; (iv) determining, by the computer-based speech translation system, whether there exists an ambiguity in the translation of the recognized speech of the first speaker in the first language into the second language; and (v) upon a determination by the computer-based speech translation system that there is ambiguity in either (a) the recognized speech of the first speaker or (b) the translation of the recognized speech of the first speaker in the first language into the second language, issuing by the computer-based speech translation system a disambiguation query to the first speaker via a user-interface of the speech translation system, wherein a response to the disambiguation query resolves the ambiguity.

In yet another general aspect, the present invention is directed to a device for extracting information from a human-to-human dialog between at least a first speaker and a second speaker. The device may comprise: at least one microphone; a screen display; and at least one programmable processor and at least one data storage unit for storing digital data. The at least one programmable processor is in communication with the screen display and the at least one microphone. And the at least one programmable processor may be programmed to:
(i) automatically recognize speech by the first and second speakers, received by the at least one microphone, during a dialog between the first and second speakers; (ii) output recognized speech of the first and second speakers on a first portion of a graphical user interface that is displayed on the screen display during the dialog between the first and second speakers; and (iii) output on a second portion of the graphical user interface that is displayed on the screen display a form with information extracted from the dialog between the first and second speakers. The at least one programmable processor may be further programmed to extract information from the dialog between the first and second speakers for outputting on the second portion of the graphical user interface in the form. Also, for a situation where the first speaker is speaking a first language and the second speaker is speaking a second language, the at least one programmable processor may be programmed to: (i) translate the recognized speech of the first speaker to the second language; (ii) translate the recognized speech of the second speaker to the first language; and (iii) display on the first portion of the graphical user interface the translations of the recognized speech of the first and second speakers. In addition, the at least one programmable processor may be programmed to recognize and received an edit to extracted information input via the screen display by a user of the device.

It will be apparent to one of ordinary skill in the art that at least some of the embodiments described herein may be implemented in many different embodiments of software, firmware, and/or hardware. The software and firmware code may be executed by a processor circuit or any other similar computing device. The software code or specialized control hardware that may be used to implement embodiments is not limiting. For example, embodiments described herein may be implemented in computer software using any suitable computer software language type, using, for example, conventional or object-oriented techniques. Such software may be stored on any type of suitable computer-readable medium or media, such as, for example, a magnetic or optical storage medium. The operation and behavior of the embodiments may be described without specific reference to specific software code or specialized hardware components. The absence of such specific references is feasible, because it is clearly understood that artisans of ordinary skill would be able to design software and control hardware to implement the embodiments based on the present description with no more than reasonable effort and without undue experimentation.

Moreover, the processes associated with the present embodiments may be executed by programmable equipment, such as computers or computer systems and/or processors. Software that may cause programmable equipment to execute processes may be stored in any storage device, such as, for example, a computer system (nonvolatile) memory, an optical disk, magnetic tape, or magnetic disk. Furthermore, at least some of the processes may be programmed when the computer system is manufactured or stored on various types of computer-readable media.

It can also be appreciated that certain process aspects described herein may be performed using instructions stored on a computer-readable medium or media that direct a computer system to perform the process steps. A computer-readable medium may include, for example, memory devices such as diskettes, compact discs (CDs), digital versatile discs (DVDs), optical disk drives, or hard disk drives. A computer-readable medium may also include memory storage that is physical, virtual, permanent, temporary, semipermanent, and/or semitemporary.

A "computer," "computer system," "host," "server," or "processor" may be, for example and without limitation, a processor, microcomputer, minicomputer, server, mainframe, laptop, personal data assistant (PDA), wireless e-mail device, cellular phone, pager, processor, fax machine, scanner, or any other programmable device configured to transmit and/or receive data over a network. Computer systems and computer-based devices disclosed herein may include memory for storing certain software modules or engines used in obtaining, processing, and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable media. The software modules and engines described herein can be executed by the processor (or processors as the case may be) of the computer devices that access the memory storing the modules.

In various embodiments disclosed herein, a single component may be replaced by multiple components and multiple components may be replaced by a single component to perform a given function or functions. Except where such substitution would not be operative, such substitution is within the intended scope of the embodiments. Any servers described herein, for example, may be replaced by a "server farm" or other grouping of networked servers (such as server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand and/or providing backup contingency in the event of component failure or reduction in operability.

The computer systems may comprise one or more processors in communication with memory (e.g., RAM or ROM) via one or more data buses. The data buses may carry electrical signals between the processor(s) and the memory. The processor and the memory may comprise electrical circuits that conduct electrical current. Charge states of various components of the circuits, such as solid state transistors of the processor(s) and/or memory circuit(s), may change during operation of the circuits.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

What is claimed is:

1. A method comprising:
   receiving a first speech input from a first speaker;
   determining, by a speech translation system, a first recognized speech result based on the speech input;
   determining, by the speech translation system, whether there exists a recognition ambiguity in the first recognized speech result, wherein the recognition ambiguity indicates more than one possible match for the first recognized speech result;
   upon a determination that there is recognition ambiguity in the first recognized speech result of the first speaker, determining a confidence score based on the recognition ambiguity; and
   responsive to the confidence score being below a threshold, issuing a first disambiguation query to the first speaker via the speech translation system, wherein a response to the first disambiguation query resolves the recognition ambiguity.

2. The method of claim 1, further comprising:
   receiving a second speech input from a second speaker;
   determining, by the speech translation system, a second recognized speech result based on the second speech input;
   extracting information from the second recognized speech input from the second speaker;
   entering the extracted information into an electronic form; and
   displaying the electronic form.

3. The method of claim 2, wherein the determination of whether there exists an ambiguity in the recognized speech result of the first speaker is based one or more of:
   an acoustic confidence score in the recognized speech result of the first speaker;
   a context of the electronic form; and
   a language context given by a translation of one or more utterances from the second speaker from a second language to the first language.

4. The method of claim 2, further comprising:
   determining, by the speech translation system, whether there exists a recognition ambiguity in the second recognized speech result of the second speaker, wherein the recognition ambiguity indicates more than one possible match for the second recognized speech result;
   upon a determination that there is recognition ambiguity in the second recognized speech result of the first speaker, determining a confidence score based on the recognition ambiguity; and
   responsive to the confidence score being below a threshold, issuing a second disambiguation query to the second speaker via the speech translation system, wherein a response to the second disambiguation query resolves the recognition ambiguity.

5. The method of claim 2, wherein the second speaker speaks a second language, further comprising:
   translating the first recognized speech result into the second language; and
   translating the second recognized speech result into the first language,
   wherein the information is extracted from the translation of the second recognized speech result.

6. The method of claim 5, wherein extracting information from the second recognized speech input from the second speaker comprises parsing the translation by a semantic grammar.

7. The method of claim 5, wherein extracting information from the second recognized speech input from the second speaker comprises detecting one or more keywords in the translation.

8. The method of claim 2, further comprising:
   retrieving one or more documents related to the extracted information from a remote database.

9. The method of claim 2, further comprising:
   soliciting feedback from at least one of the first speaker and the second speaker prior to entering the extracted information into the electronic form.

10. The method of claim 2, further comprising:
    receiving an edit to the extracted information in the electronic form; and
    updating the electronic form to reflect the received edit.

11. A non-transitory computer-readable medium comprising instructions that when executed by a processor cause the processor to:
receive a first speech input from a first speaker;
determine, by a speech translation system, a first recognized speech result based on the speech input;
determine, by the speech translation system, whether there exists a recognition ambiguity in the first recognized speech result, wherein the recognition ambiguity indicates more than one possible match for the first recognized speech result;
upon a determination that there is recognition ambiguity in the first recognized speech result of the first speaker, determine a confidence score based on the recognition ambiguity; and
responsive to the confidence score being below a threshold, issue a first disambiguation query to the first speaker via the speech translation system, wherein a response to the first disambiguation query resolves the recognition ambiguity.

12. The non-transitory computer-readable medium of claim 11, further comprising instructions that cause the processor to:
receive a second speech input from a second speaker;
determine, by the speech translation system, a second recognized speech result based on the second speech input;
extract information from the second recognized speech input from the second speaker;
enter the extracted information into an electronic form; and
display the electronic form.

13. The non-transitory computer-readable medium of claim 12, wherein the determination of whether there exists an ambiguity in the recognized speech result of the first speaker is based one or more of:
an acoustic confidence score in the recognized speech result of the first speaker;
a context of the electronic form; and
a language context given by a translation of one or more utterances from the second speaker from the second language to the first language.

14. The non-transitory computer-readable medium of claim 12, further comprising instructions that cause the processor to:
determine, by the speech translation system, whether there exists a recognition ambiguity in the second recognized speech result of the second speaker, wherein the recognition ambiguity indicates more than one possible match for the second recognized speech result;
upon a determination that there is recognition ambiguity in the second recognized speech result of the first speaker, determine a confidence score based on the recognition ambiguity; and
responsive to the confidence score being below a threshold, issue a second disambiguation query to the second speaker via the speech translation system, wherein a response to the second disambiguation query resolves the recognition ambiguity.

15. The non-transitory computer-readable medium of claim 12, wherein the second speaker speaks the second language, further comprising instructions that cause the processor to:
translate the first recognized speech result into a second language; and
translate the second recognized speech result into the first language,
wherein the information is extracted from the translation of the second recognized speech result.

16. The non-transitory computer-readable medium of claim 15, wherein the instructions to extract information from the second recognized speech input from the second speaker comprise instructions to parse the translation by a semantic grammar.

17. The non-transitory computer-readable medium of claim 15, wherein the instructions to extract information from the second recognized speech input from the second speaker comprise instructions to detect one or more keywords in the translation.

18. The non-transitory computer-readable medium of claim 12, further comprising instructions that cause the processor to:
retrieve one or more documents related to the extracted information from a remote database.

19. The non-transitory computer-readable medium of claim 12, further comprising instructions that cause the processor to:
solicit feedback from at least one of the first speaker and the second speaker prior to entering the extracted information into the electronic form.

20. The non-transitory computer-readable medium of claim 12, further comprising instructions that cause the processor to:
receive an edit to the extracted information in the electronic form; and
update the electronic form to reflect the received edit.

* * * * *